United States Patent

Markelov

[11] Patent Number: 5,932,482
[45] Date of Patent: Aug. 3, 1999

[54] HEADSPACE VIAL APPARATUS AND METHOD

[76] Inventor: Michael Markelov, 7276 Greenfield Trail, Chesterland, Ohio 44026

[21] Appl. No.: 09/131,291

[22] Filed: Aug. 10, 1998

[51] Int. Cl.$^6$ .................................................. G01N 1/22
[52] U.S. Cl. ............................................. 436/181; 422/102
[58] Field of Search ............................. 422/83, 89, 102, 422/82; 436/181, 161

[56] References Cited

U.S. PATENT DOCUMENTS

| | | | |
|---|---|---|---|
| 4,248,355 | 2/1981 | Kolb et al. | 215/274 |
| 5,344,780 | 9/1994 | Nonboe | 436/21 |
| 5,356,814 | 10/1994 | Carrico, Jr. et al. | 435/286 |
| 5,458,113 | 10/1995 | Burns | 128/763 |
| 5,516,692 | 5/1996 | Berndt | 435/286.7 |
| 5,567,309 | 10/1996 | Classon et al. | 210/233 |
| 5,580,530 | 12/1996 | Kowatch et al. | 422/102 |
| 5,711,786 | 1/1998 | Hinshaw | 95/82 |
| 5,732,476 | 3/1998 | Pare | 34/265 |
| 5,750,075 | 5/1998 | Spike | 422/10 |
| 5,792,423 | 8/1998 | Markelov | 422/83 |
| 5,827,944 | 10/1998 | Nickerson | 73/23.41 |
| 5,849,505 | 12/1998 | Guirguis | 435/7.2 |

*Primary Examiner*—Jill Warden
*Assistant Examiner*—Paul J. Lee
*Attorney, Agent, or Firm*—Ralph E. Jocke

[57] ABSTRACT

A headspace autosampling apparatus (92) for generating and delivering gaseous samples to a gas chromatograph or other instrument. The vials are delivered one at a time through a vial delivery mechanism (160) to a heated zone (146) wherein the substances (94, 96) to be analyzed reach equilibrium with the headspace (100, 102) above the samples in the vials. The vials are generally cylindrical and extend horizontally to facilitate attainment of equilibrium rapidly upon heating. The vials are also preferably rotated about their longitudinal axis prior to sampling so as to achieve a film effect on the interior walls of the vials which further aids in attainment of equilibrium. The apparatus is operative to first pressurize the headspace in the vial with an inert gas, and then to place said headspace in fluid communication with the inlet of a gas chromatograph wherein analyses in the headspace volume are analyzed to determine the composition thereof. One form of vial (260) operates to minimize changes in amounts of materials in the sample due to changes in equilibrium during sampling.

26 Claims, 10 Drawing Sheets

HEADSPACE VIAL APPARATUS AND METHOD

TECHNICAL FIELD

This invention relates to analysis of materials. Specifically, this invention relates to a headspace autosampler apparatus for generating and delivering gaseous samples to an analytical instrument such as a gas chromatograph, and a vial for use in holding a substance for analysis.

BACKGROUND ART

Gas chromatography is an advantageous method for analyzing minute quantities of complex mixtures from biological and chemical sources. Gas chromatography may be used to determine the constituents in the mixture from which the sample is taken. Gas chromatography typically involves volatilizing a sample to be analyzed and moving the sample in a stream of inert carrier gas.

The sample and carrier gas are delivered to a packing bed or column in the gas chromatograph. The different constituents in the sample move through the column at different rates. As a result, they are separated and appear one after the other at the output end of the column. At the outlet end the separated materials in the sample are identified through their properties of thermoconductivity, density differences or by ionization detectors, depending on the analyzer type in the gas chromatograph.

Headspace sampling is a technique that involves testing a gaseous sample generated in a closed container above a solid or liquid phase of the substance to be analyzed. Sampling gaseous material avoids the introduction of non-volatile or solid particles or substances which cannot be volatilized into the inlet of the gas chromatograph, which is not desirable.

Headspace sampling in accordance with the present invention optimally involves establishing an equilibrium in a sealed vial between a solid or liquid phase of a substance to be analyzed and a vapor phase of the substance. The vapor phase occupies the headspace volume above the other phase. Equilibrium is established by heating or cooling the sample in the vial. A gaseous sample is then taken from the headspace and delivered to the analytical instrument.

Headspace sampling in general has advantages because it assures that only gaseous material enters the gas chromatograph or other analytical instrument. Further, because the sample is vapor, the amount of the sample may be much larger than a liquid sample. This increases the sensitivity of the analysis. These advantages of headspace sampling make it a useful technique in the analysis of polymers, latexes, paints, foods, biological materials, environmental samples, pharmaceuticals, fragrances and other substances.

Headspace sampling techniques used in the prior art have certain limitations. First, the volatility of a particular substance at a given temperature varies depending on the matrix of other materials it is mixed with. For example, the same concentration of benzene in water versus benzene in gasoline will provide very different concentrations of benzene in a headspace at the same temperature. Therefore, in the prior art, it has been necessary to prepare calibration samples to simulate the matrix of materials in the substance being analyzed. However, this is impossible in cases of a solid sample or a substance that is completely unknown.

A further drawback of prior art headspace sampling techniques is that it takes some samples a long time to reach equilibrium between the condensed and vapor phases. Achieving equilibrium with prior art equipment often requires hours of heating. This is particularly true for viscous or solid substances. Some have tried agitation of the sample and vial in an attempt to shorten equilibrium times, but this has not proven effective and sometimes causes contamination problems.

Several approaches to headspace sampling are known in the prior art. Each of these approaches suffers the drawback that removal of the gaseous sample from the headspace disturbs the equilibrium in the headspace. Such disturbance of the equilibrium can cause poor repeatability. A further problem common to prior art techniques is that a disturbance in equilibrium may vary from sample to sample depending on the technique used and the properties of the materials being analyzed.

One approach to headspace sampling used in the prior art is syringe sampling. This technique involves removing a sample of gaseous material from the headspace volume above a substance to be analyzed, using a syringe. The disturbance of the equilibrium in the headspace using this technique depends on the amount of headspace in the sample vial compared to the volume of the sample removed from the headspace. It also depends on the speed of removal of the sample, as removal of the material from the headspace will tend to cause more of the substance to enter the vapor phase to establish a new equilibrium.

A further problem with the syringe technique is that when the syringe is removed from the vial, some of the vapor will expand and escape from the syringe to atmosphere prior to injection of the sample into the inlet port which carries the sample into the column of the gas chromatograph, or other instrument. Another drawback is that material in the sample may begin to condense on the surfaces of the syringe before the sample enters the gas chromatograph. As a result, not all the material in the sample may be delivered, which causes poor repeatability.

Another headspace sampling technique used in the prior art is explained with reference to FIG. 1. This approach is called fixed volume injection. The fixed volume system 10 has a sample vial 12 with a substance 14 therein. The vial is generally a cylindrical vial which is held in the generally upright position during sampling. This is standard with prior art headspace sampling techniques.

A sampling needle 16 is positioned in the headspace inside the vial above the substance. The needle is in fluid communication with a first port 20 of a six port valve 22. Six port valve 22 alternatively places first adjacent ports, shown connected by the solid lines in the drawing, in fluid communication when the valve is in a first condition. In a second condition of the valve, the alternative adjacent ports shown connected by the dashed lines are connected.

The second and fifth ports of the valve 24 and 26, respectively, are connected by a sample loop 27. The third port 28 is connected to the inlet of the gas chromatograph. The fourth port 30 is connected to a source of inert carrier gas such as helium. The sixth port 32 is connected to a valve 34 that is alternatively connected to a source of inert gas or to atmosphere.

In operation, with valve 22 in the condition shown in the drawing, the inert gas pressure of port 32 is applied to headspace 18 through port 20. In this condition of valve 22, the carrier gas passes through the sample loop 27 to the gas chromatograph inlet through ports 30, 26, 24 and 28.

The conditions of valves 22 and 34 are then changed. In these alternative conditions, the headspace sample is directed into the sample loop through connection of ports 20 and 24 of the valve.

The sample loop 27 also vents to atmosphere due to the connection of ports 26 and 32 and the opening of valve 34. As a result, sample loop 27 is filled with gaseous material from the headspace of the vial.

The return of valve 22 to the first condition causes the carrier gas to wash the sample material in the sample loop into the inlet of the gas chromatograph. This is accomplished because the carrier gas is connected to port 26 and pushes the material in the sample loop through ports 24 and 28.

The operation of the system 10 includes several timed functions including the time of heating the sample to attempt to achieve equilibrium, pressurization time for the headspace, time of venting the headspace vapors through the sample loop and the time of washing the sample loop with the carrier gas. The times are preset based on estimates of what may be appropriate. In many instances the preset times are totally inappropriate for a given sample. All of these timed event functions impact the results produced by the gas chromatograph.

Also problematic is that venting the sample to atmosphere disturbs the headspace equilibrium. Another common problem is that the headspace vapor passing through the lines and valves of the system begins to condense resulting in failure to transmit all the constituents of the sample to the analytical instrument. This further adversely affects repeatability and cross contamination between samples.

An alternative type of prior art headspace sampling system 36 is shown in FIG. 2. In this system, a vial 38 contains a substance 40 to be analyzed. The headspace 42 is pressurized with carrier gas through a sampling needle 44. At the same time as the headspace is pressurized, the column of the connected gas chromatograph 46 is pressurized to the same pressure. Carrier gas flow to the vial and to the gas chromatograph is then shut off. Thereafter the headspace 42 of the vial is the source of gas delivered to the gas chromatograph.

This type of sampling is suitable for use with gas chromatographs or other instruments that have high column pressures. However, many gas chromatographs have low column pressures which make this prior art approach unsuitable. This is because at low pressures the amount of sample delivered into the column of the gas chromatograph is too small to produce accurate results.

In conclusion, prior art sampling devices have inherent problems due to the effects of condensation or loss of the constituents of the sample before entry into the gas chromatograph. Prior art systems also have the drawback that long heating times are required to insure that the headspace reaches equilibrium with the other phase of the substance to be analyzed and often the equilibrium is not achieved. Prior art systems further have the drawback that the fixed machine cycle times for the sampling device are not appropriate for the sample, resulting in loss of repeatability.

Thus there exists a need for a headspace autosampling apparatus that provides greater sensitivity and repeatability, reduces cycle times and is readily adaptable for use with a variety of substances and types of analytical instruments. There further exists a need for a vial for use in connection with a headspace sampling apparatus that reduces the effect of the sampling process on the equilibrium in the vial between the vapor phase and the non-vapor phase of the substance for analysis.

DISCLOSURE OF INVENTION

It is an object of the present invention to provide a headspace autosampling apparatus that provides high sensitivity with greater repeatability.

It is a further object of the present invention to provide a headspace autosampling apparatus that provides reduced cycle times and faster sample turnaround.

It is a further object of the present invention to provide a headspace autosampling apparatus that is capable of automatically handling a large number of samples.

It is a further object of the present invention to provide a headspace autosampling apparatus that is compact and which can be mounted directly on a gas chromatograph or other analytical instrument.

It is a further object of the present invention to provide a headspace autosampling apparatus that is suitable for use with a wide range of sample types.

It is a further object of the present invention to provide a headspace autosampling apparatus that is suitable for use with a variety of gas chromatography and other analytical units.

It is a further object of the present invention to provide a headspace autosampling apparatus that is adapted for use with full evaporation technique (FET) headspace analysis.

It is a further object of the present invention to provide a headspace autosampling apparatus that employs sample vials that are adapted for robotic handling.

It is a further object of the present invention to provide a headspace autosampling apparatus that includes a manual sample injection port that enables manual injection of samples without loss of sensitivity.

It is a further object of the present invention to provide a headspace autosampling apparatus that may be operated under flexible programmable control, that simplifies method development, enables optimization of headspace conditions and provides greater repeatability.

It is a further object of the present invention to provide an apparatus which performs both purge and trap analysis and headspace analysis.

It is a further object of the present invention to provide a headspace autosampling apparatus that provides for manual override of operations in the machine cycle.

It is a further object of the present invention to provide a headspace autosampling apparatus that is reliable and has simplified maintenance and diagnostic characteristics.

It is a further object of the present invention to provide a vial for use in connection with a headspace autosampler apparatus.

It is a further object of the present invention to provide a vial for use in connection with a headspace autosampler apparatus that reduces the changes in equilibrium between the vapor phase and the non-vapor phase of a substance being analyzed during the sampling process.

It is a further object of the present invention to provide a vial that when used in connection with a headspace sampling apparatus achieves improved sensitivity and repeatability of analysis.

It is a further object of the present invention to provide a method of sampling a vapor phase of a substance for analysis with an analytical instrument.

It is a further object of the present invention to provide a method of sampling a substance for analysis with an analytical instrument that provides enhanced sensitivity and repeatability.

Further objects of the present invention will be made apparent in the following Best Modes for Carrying Out Invention and the appended claims.

The foregoing objects are accomplished in the preferred embodiment of the present invention by headspace autosampling apparatus that includes a plurality of vials for holding substances to be analyzed. The vials are generally cylindrical and are vertically arranged in stacks with the longitudinal axis of the vials extending generally horizontally.

The vials are fed from a stack into a heated or cooled temperature controlled zone inside the apparatus. Ideally the heating or cooling results in the substance having both a liquid and vapor phase in the vial. Because of the large surface area interface between the liquid sample and the headspace volume in the vials due to the generally horizontal vial orientation, equilibrium between the liquid substance and the headspace is rapidly achieved. In addition, the vial is optimally rotated about its longitudinal axis which causes a liquid film of the substance to be deposited on the wall of the vial bounding the headspace. This further increases the surface area and facilitates achieving equilibrium between the vapor phase of the substance in the headspace and the non-vapor phase, and reduces the time necessary to achieve equilibrium.

The apparatus then preferably pressurizes the headspace through a pressurization line. The headspace volume is pressurized to a predetermined pressure or flow using a flow needle. An inert gas is used to pressurize the headspace. The gas temperature is carefully controlled and is maintained at the same temperature as the vials so as to minimize the upset in the equilibrium in the headspace. Thereafter, the pressure in the headspace is relieved to the inlet of a gas chromatograph or other instrument, through valving and lines that are also carefully temperature controlled. Thereafter, the sample is washed into the inlet of the gas chromatograph using a carrier gas. The temperature of the carrier gas is also controlled to avoid condensation, and its path through the apparatus assures that all of the sample is analyzed.

The preferred form of the invention is used in connection with sample holding vials that help reduce the effects of sampling on the equilibrium between a vapor phase and a non-vapor phase of the substance for analysis held in the vial. The vial includes a dividing member which separates a first portion of an interior area of the vial from a second portion of the interior area of the vial. The non-vapor phase of the substance for analysis is contained in the first portion. A fluid passage which enables vapor to flow between the first and second portions extends through the dividing member.

A closing member is movable relative to the vial between positions opening and closing the fluid passage. During equilibration of the vapor and the non-vapor phases of the substance for analysis within the vial, the closing member is positioned so that the fluid passage is open. As a result, the vapor phase of the substance occupies the first and second portions of the interior area of the vial.

When a sample needle is inserted into the second portion of the interior area, the closing member is moved to close the fluid passage. As a result, the non-vapor phase is isolated from the vapor phase of the substance in the second portion, generally before pressure changes in the second portion associated with extracting the vapor sample can change the equilibrium between the vapor phase and the non-vapor phase of the substance. As a result, the influence of the sampling process on the makeup of the vapor sample extracted from the vial is reduced.

The preferred form of headspace autosampling apparatus of the present invention is adapted to run samples continuously and to accumulate data on a large number of samples without the need for reloading or reprogramming. The preferred embodiment of the invention includes several functional features to insure accuracy, safety and repeatability of the sampling process. The preferred embodiment of the invention is particularly well adapted for headspace analysis using a technique known as full evaporization technique (FET) which enables minimization of matrix effects.

BEST MODES FOR CARRYING OUT INVENTION

Figure 1:
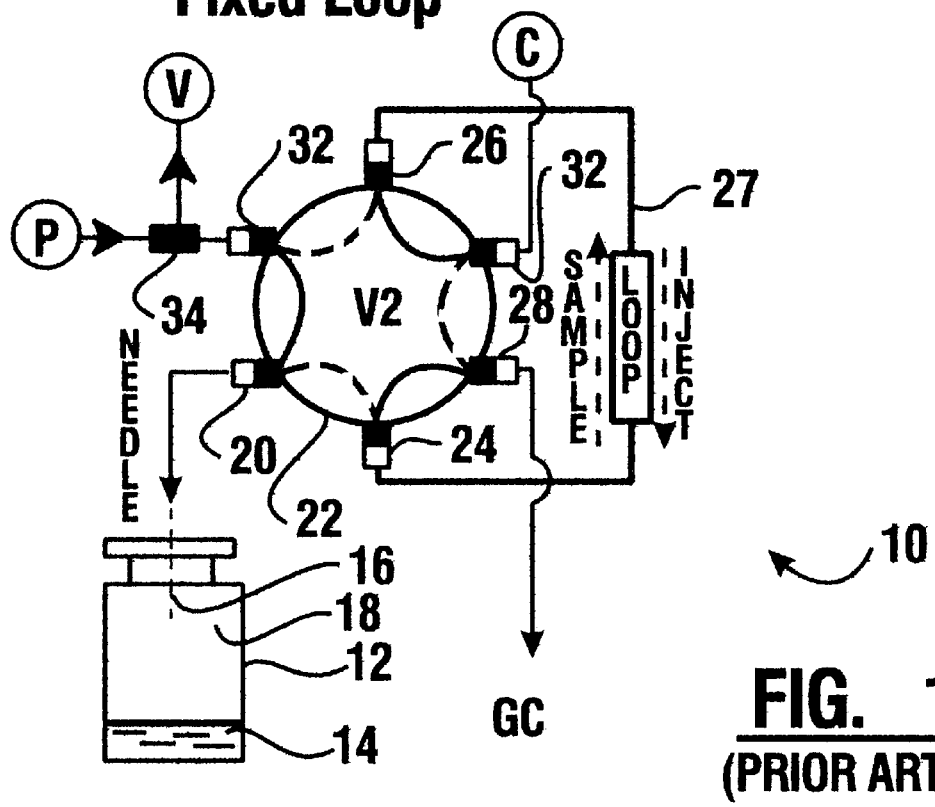
FIG. 1 is a schematic view of a fixed loop prior art headspace sampling system previously discussed.
Figure 2:
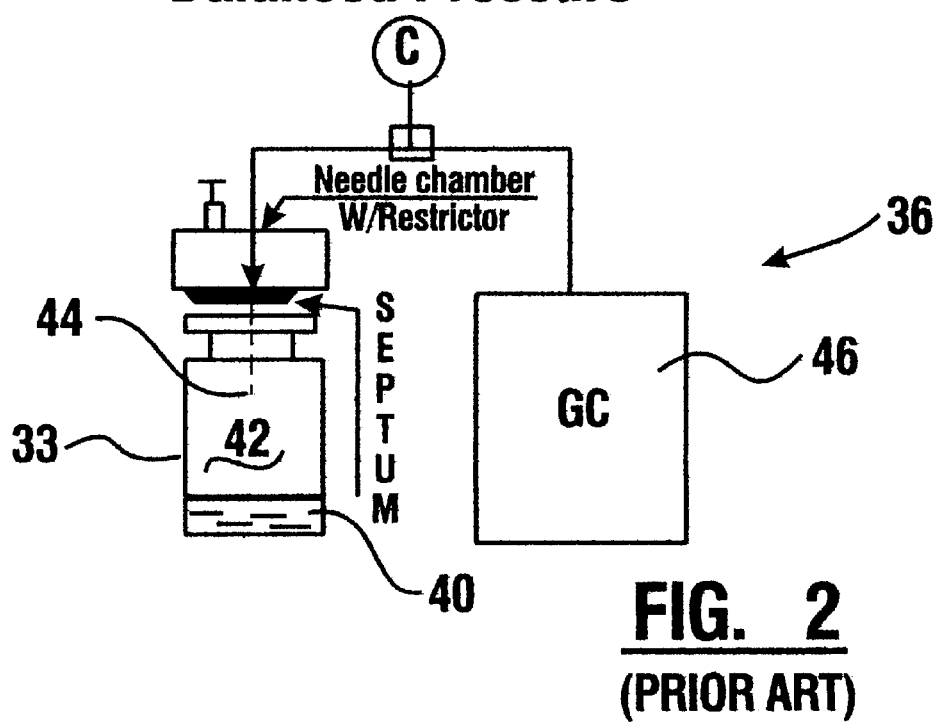
FIG. 2 is a schematic view of a balance pressure prior art headspace sampling system previously discussed.
Figure 3:
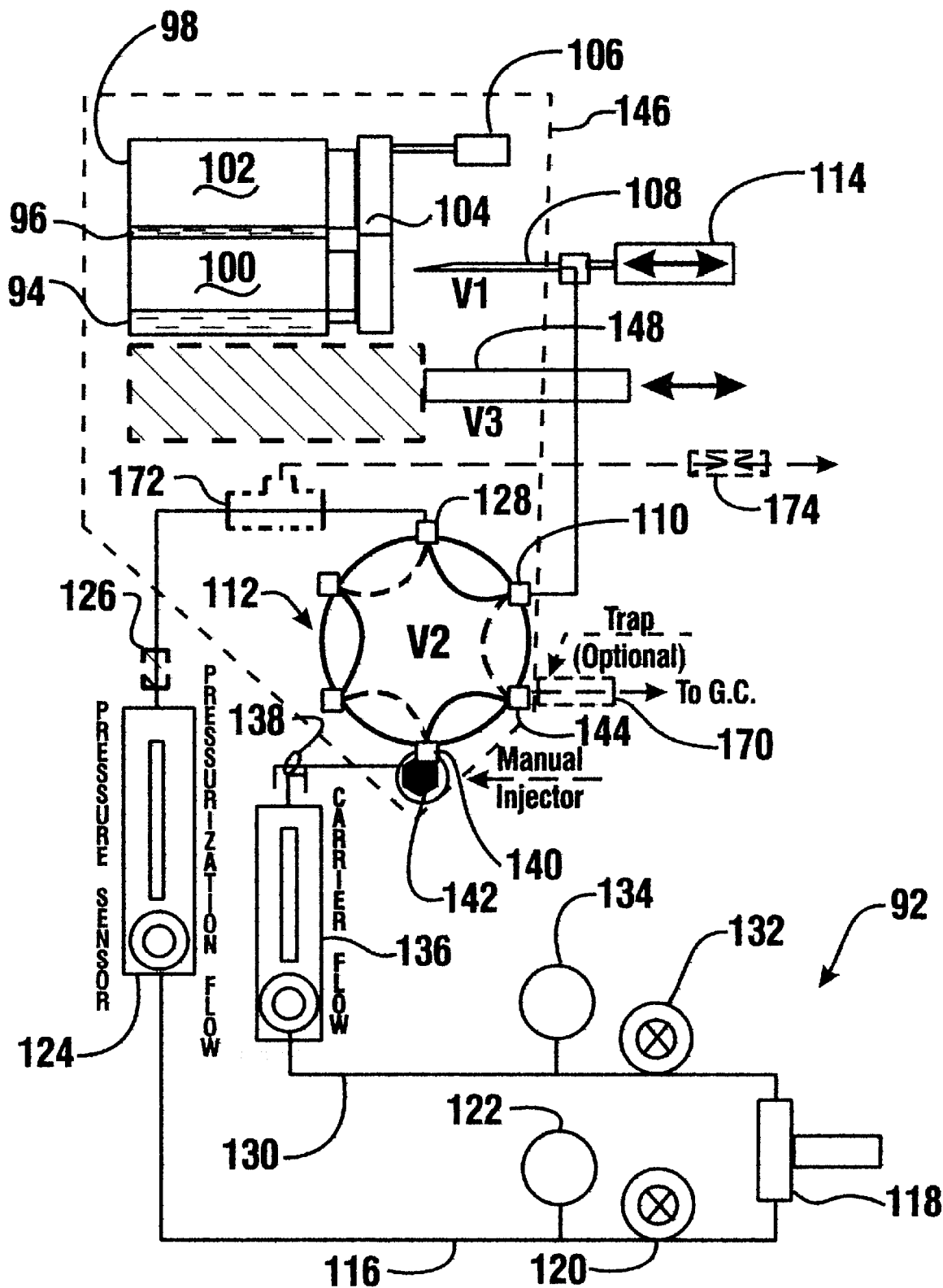
FIG. 3 is a schematic view of a headspace autosampling apparatus of one preferred embodiment of the present invention.

Referring now to the drawings and particularly to FIG. 3, there is shown therein a schematic view of one preferred embodiment of a headspace autosampling apparatus of the present invention, generally indicated 92. The apparatus is adapted for sampling substances 94, 96 located in identical vials 98. The vials of the preferred embodiment are generally cylindrical and are configured to have a horizontal dimension greater than a vertical dimension. Each vial 98 has an interior volume which defines a headspace 100, 102 above the substances therein 94, 96, respectively.

Figure 9:
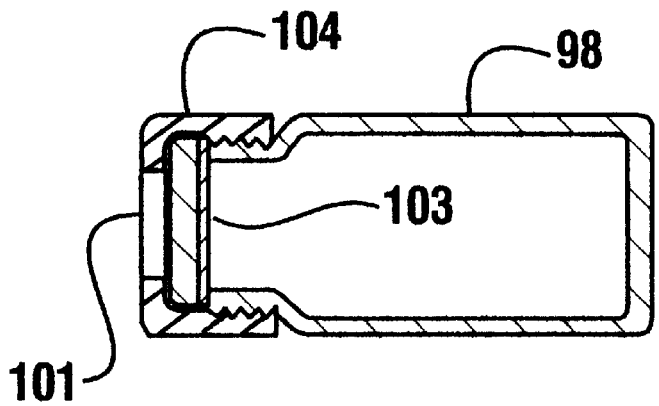
FIG. 9 is a cross sectional view of one form of a sample vial used in connection with the preferred embodiment of the invention.

Vials 98 include removable caps 104 at a first axial end of the vials (see FIG. 9). A silicone membrane or septum 101 extends across an opening in each cap. In the preferred embodiment the septum includes a layer 103 of inert material at its interior surface. In the preferred embodiment the layer is 10–20 mils of Tetrafluoroethylene (TFE). The membrane is preferably about 125 mils in thickness. The vial is preferably about 2.5 inches long and 1.125 inches in outside diameter, with an internal volume of 25 milliliters.

Figure 7:
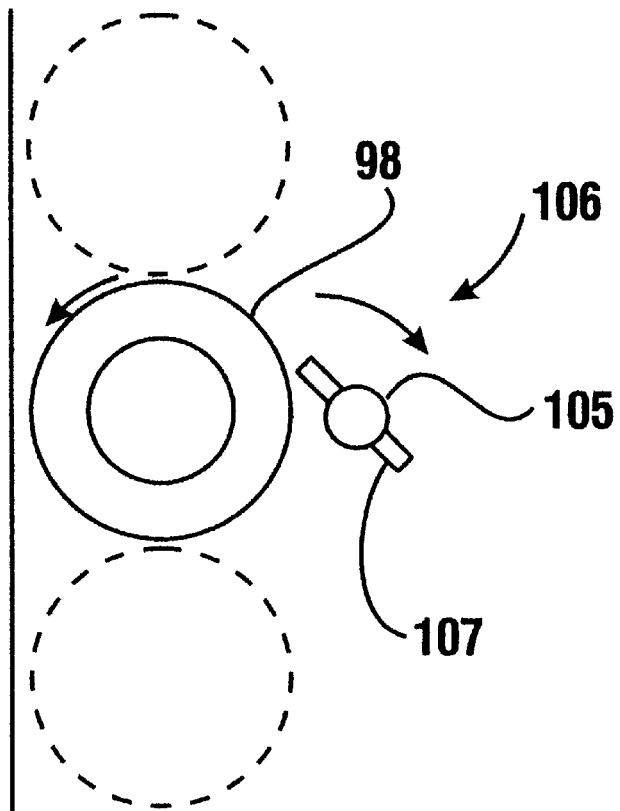
FIG. 7 is a side view of sample vials in the passage of the headspace sampling apparatus, and the vial rotation mechanism.
Figure 8:
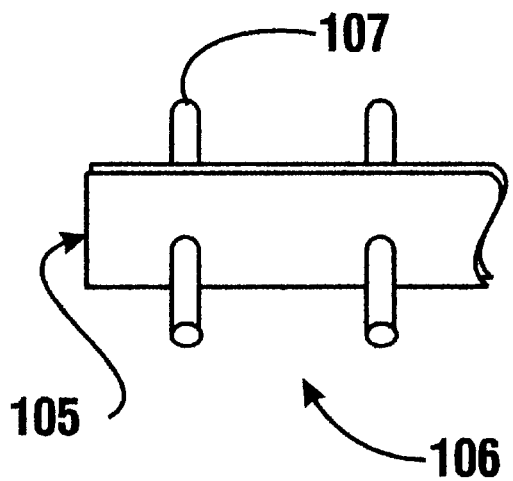
FIG. 8 is a right side view of the vial rotation mechanism shown in FIG. 7.

A rotating device 106 is adapted for rotating vials 98 about the longitudinal axis prior to sampling. As shown in FIGS. 7 and 8 the preferred embodiment of the rotating device 106 preferably includes a slowly rotating shaft 105. Shaft 105 has a plurality of radially extending flexible rubber rods 107 extending therefrom. The rods engage the cylindrical side of the vial during each rotation to rotate the adjacent vial as shown. Of course in alternative embodiments any type of rotating device or other vial moving device suitable for coating the walls of the vial with a film of the sample in the manner discussed hereafter may be used.

The vials are enabled to move downward past rotating rods 107 by force of gravity. Of course in other embodiments other means of moving the vials may be employed including powered vial conveying devices.

In the apparatus as schematically shown in FIG. 3, a sample needle, which is also referred to herein as a flow needle 108, is in fluid communication with a port 110 of a six port valve 112. Flow needle 108 is mounted in connection a horizontal actuator 114 such as a solenoid plunger. When actuator 114 moves inward toward the adjacent vial, the flow needle pierces the septum 101 and is placed in fluid communication with the headspace 100 and serves as a conducting device for conducting the sample out of the headspace. The flow needle 108 is preferably somewhat above center of the longitudinal axis of the adjacent vial. This helps to assure that the flow needle is disposed vertically above the level of the substance 94 located on the lower side of the vial.

A pressurization line 116 is connected to a source 118 of inert gas which is preferably helium. Pressurization line 116 includes a regulator 120 and has a pressure gauge 122 thereon. Pressurization line 116 includes a first flow meter 124 as well as a pressure sensor 126 therein. Pressurization line 116 is connected to a port 128 of the six port valve 112. Flowmeter 124 in the preferred embodiment gives a visual as well as an electrical indication of the flow condition of the gas passing therethrough as hereinafter explained.

A carrier gas line 130 is also connected to the source 118 of inert gas. The carrier gas line includes a pressure regulator 132 and a pressure gauge 134 therein. Carrier gas line 130 includes a second flowmeter 136 and a pressure release valve 138. Carrier gas line 130 is connected to a port 140 of valve 112. Carrier gas line 130 also includes therein a manual injection port 142 adjacent to port 140 of the valve.

Valve 112 includes a port 144 which is in fluid communication with an inlet of a gas chromatograph or other analytical instrument. As shown schematically in FIG. 3, the vials 98, the flow needle 108, valve 112 and the pressurization and carrier lines 116 and 130 are all housed in a temperature controlled zone 146 in the apparatus 92. The temperature of the temperature controlled zone 146 is maintained by a heat transfer device which includes suitable heating and cooling mechanisms such as an electrical heater or heat exchanger. It should be understood that all the lines, valves, and fluid passages adapted for gas flow in the temperature controlled zone are preferably maintained at temperatures consistent with that of the headspace of the vials to be sampled. This assures that there is no condensation of any material from the sample in the lines that would result in loss of sample material and reduces the amount the equilibrium condition in the vial is upset during the sampling processes.

With samples that are liquids at room temperature, the temperature controlled zone operates at an elevated temperature to achieve equilibrium between the liquid sample and the headspace. For substances that are gases at room temperature the temperature controlled zone is operated to cool and condense a liquid sample portion. Of course, samples that are in a solid phase may also be used.

The apparatus further includes any ejection plunger 148. Ejection plunger 148 is movable to eject vials from the apparatus after the headspace therein is sampled. The ejection plunger is operated in the preferred embodiment by a solenoid actuator to eject the vials from the heated zone. After a vial is ejected, it may fall outward into a basket or other container. When the ejection plunger is retracted, the vials above it fall downward in a passage which holds the vials in the temperature controlled zone in vertical alignment as shown in FIG. 7. The passage assures that the vial previously sampled is in position for ejection while the vial positioned immediately above it in the passage is in position for sampling. This arrangement further provides that the vial immediately above the vial in position for sampling is rotated by rotating device 106. Preferably the vial above the vial in direct contact with the rotating device is rotated as a result of being in contact with the rotating vial.

The device of the preferred embodiment heats (or cools) the vials and samples the headspace of one vial at a time. However, in other embodiments multiple vials may be transported together for heating, rotation or sampling.

Figure 5:
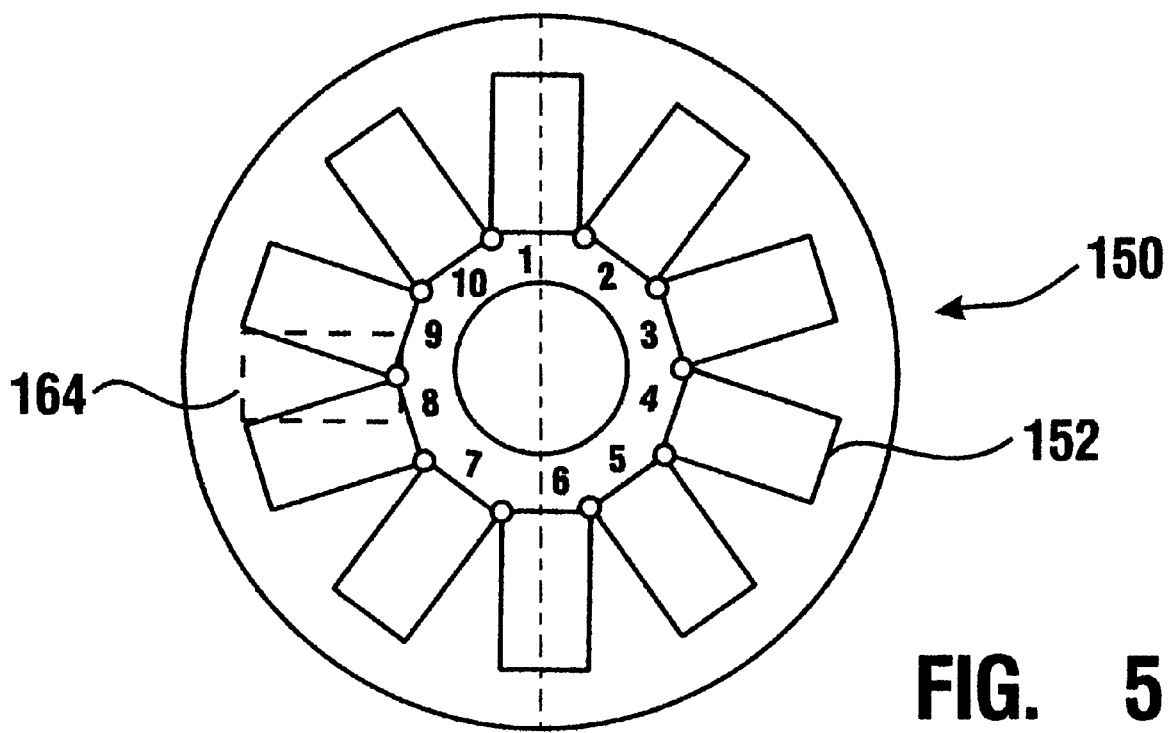
FIG. 5 is a top plan view of the carousel for holding sample vials of the preferred embodiment of the present invention.
Figure 6:
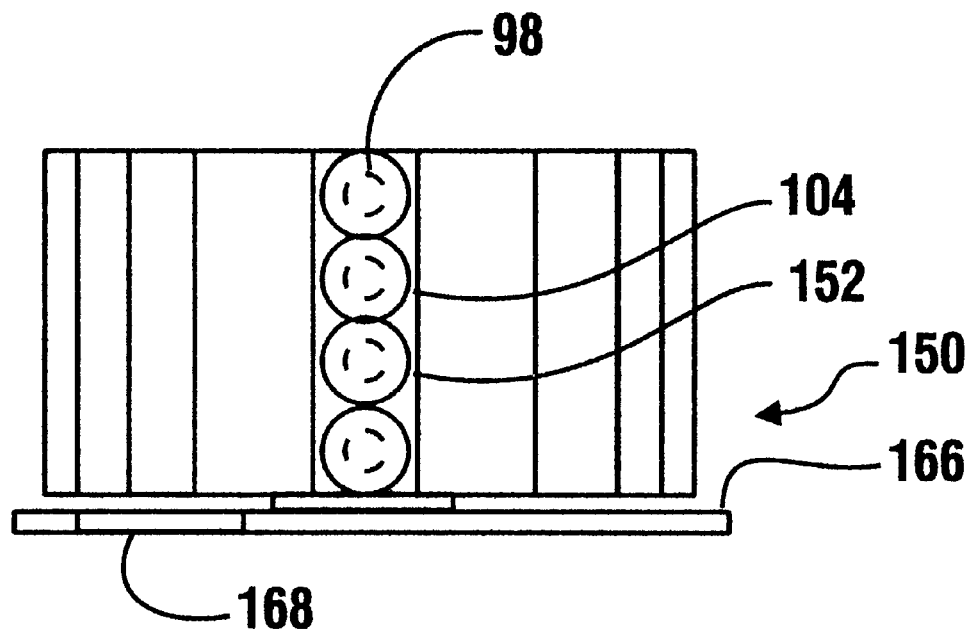
FIG. 6 is a right side view of the carousel shown in FIG. 5.

The headspace auto sampling apparatus of the preferred embodiment of the present invention is adapted for sampling various substances in large numbers of vials and on a continuous basis. In one preferred embodiment, the apparatus includes a carousel 150 (see FIGS. 5 through 6) which serves as a holding device. Carousel 150 holds a plurality of vials 98 which are vertically arranged in groups or stacks 152. The carousel is adapted for holding 10 stacks of four vials each in the preferred embodiment. When positioned in the carousel, the vials are all arranged so that their caps 104 and the rubber septums therein are outwardly directed.

Figure 4:
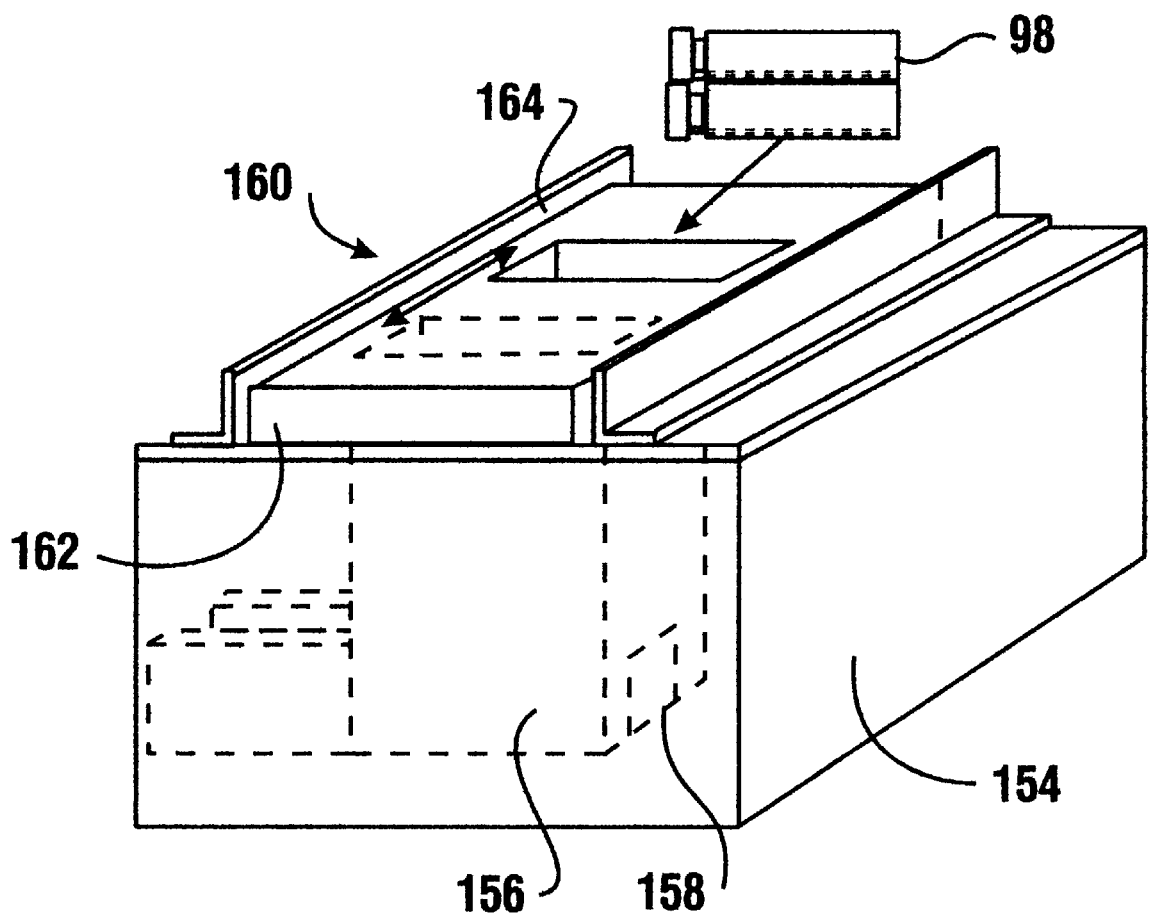
FIG. 4 is an isometric view of an oven portion and sample delivery mechanism of the preferred embodiment of the present invention.

The carousel 150 is rotationally movable by an indexing device such as a stepper motor or other type of mechanism which is operable to rotate the carousel. The indexing device is operable to rotate the carousel into a desired position for feeding the vials 98 into the delivery device for delivering the vials into the temperature controlled zone wherein they are heated (or cooled depending on the state of the sample at room temperature), rotated and sampled. The carousel 150 is mounted above a housing 154 (see FIG. 4) which includes a temperature controlled enclosure 156. Enclosure 156 encloses temperature controlled zone 146. Enclosure 156 includes a lateral opening 158 through which vials ejected by ejection plunger 148 pass out of the device. The ejection plunger is sized similar to opening 158 and is generally extended during most of the machine cycle, except when it retracts to engage a vial for ejection. As a result the ejection plunger minimizes heat transfer through the opening to help maintain a constant temperature in the temperature controlled zone.

The housing 154 includes a vial delivery mechanism 160 thereon. Mechanism 160 includes a sliding member 162 which is positioned above the temperature controlled zone. The sliding member 162 includes an aperture 164 therein. The aperture is sized for accepting a single vial 98 so that the wall bounding the vial at the top is aligned with the top of the sliding member. The sliding member 162 is movable by a feed mechanism, which in the preferred embodiment includes a solenoid, between a first aperture position shown in FIG. 4 and a second aperture position which is shown in phantom. In the first aperture position, the aperture 164 is enabled to receive a vial from one of the stacks 152 in the carousel. In a second position of the aperture, the aperture is positioned over the passage into which the vials pass into the temperature controlled zone for eventual sampling.

The sliding member 162 has a wall extending adjacent its underside so that a vial in the aperture moves in captured relation with the sliding member until the sliding member reaches the second position. In the second position the vial falls into the passage and enters the temperature controlled zone. In the second position the vial is in vertically stacked relation with other vials in the passage which are being heated (or cooled) and are awaiting sampling. The delivery mechanism 160 not only operates to deliver the vials one at a time for sampling, but also serves as a cover for the passage into the temperature controlled zone. As a result, the mechanism helps to maintain the temperature controlled zone at a stable temperature.

A sensor (not separately shown) is also positioned in the housing 154 adjacent the aperture in the first position. The sensor, which is preferably a photo sensor, is adapted for sensing when no vials remain in a group. In this condition the control logic of the apparatus causes the carousel to rotate until the next group is over the aperture. A programmed controller which controls the machine operates to continue rotation of the carousel until all the groups have been tried and it is determined that no additional vials are available for sampling, at which point the apparatus is shut off after the last vial in the passage is sampled.

It should be noted that carousel 150 includes a base plate 166. The base plate includes an opening 168 which corresponds to the first position of aperture 164 of the sliding member. The base plate 166 also operates to support vials 98 in the groups 152. As the carousel indexes, the bottom vials in the groups move rotationally about their longitudinal axis. This rotation also causes the vials above to rotate. This rotation during indexing aids in producing a film effect, which causes a film of the substance to be analyzed to be deposited on the interior walls of the vials as they rotate. The film effect facilitates the attainment of equilibrium in the headspace of the vial when the vial reaches the temperature controlled zone.

The headspace autosampling apparatus of the present invention is operated under the control of a programmable controller. The controller preferably includes several built in programs stored in memory as well as the ability to be programmed with custom programs through an interface port. The control programs control the times for loading of the vial from the carousel 150 into the passage for heating or cooling. The programs also control the movement of the flow needle to pierce the septum of the vial and the condition of the six port valve. The programs also typically control the ejection plunger which operates to eject a vial after sampling.

One preferred form of the invention also includes other features in the control programs to assure safe operation and to facilitate the interface of the apparatus with a gas chromatograph or other analytical instrument. These features include temperature sensors in the temperature controlled zone 146 to insure that the unit will not operate to produce samples if the temperature in the temperature controlled zone is not within certain limits. In the event the temperature should exceed a programmed limit, the controller of the unit executes a built-in alarm program routine. This routine operates to eject all sample vials from the temperature controlled zone, and then shuts off the device. This avoids possible dangerous conditions from overheating. The apparatus also includes an interface with a gas chromatograph or other instrument which can be used to insure that the instrument is operating properly and is ready to receive samples before the autosampling unit commences operation.

Another novel aspect of the invention is a feature which allows relief of the pressure on the column of the gas chromatograph by opening a pressure release valve 138 and closing it again prior to delivering a sample. Such relief of the column pressure is desirable where the column pressure is high and may resist the infiltration of sample material, or in situations where high pressure may adversely impact sensitivity. The pressure release valve can also be used to relieve pressure in the vials after sampling as a safety precaution, in which case its outlet may be ducted to a suitable trap. Further control functions are associated with the use of a trap shown in phantom as 170 on the line leading to the inlet of the gas chromatograph which may be used for trapping and/or later delivery of constituents in the samples. Further features of the control programs provide for counting and identifying samples and for shutting off the gas chromatograph when all the samples have been sampled. The control programs are also operative to detect fault conditions and to shut off the apparatus when fault conditions are detected.

The described form of the invention provides flexibility by enabling programmed control of all the functions, as well as hard wired control through externally mounted electrical terminal strips. This enables simplification of method development and optimization of headspace conditions. The preferred form of the apparatus of the present invention also includes manual override controls for the functions performed by the unit.

In operation, the headspace autosampling apparatus of the present invention operates to deliver gaseous samples to an inlet of a gas chromatograph or other analytical instrument in the ways hereinafter described. The apparatus is first allowed to heat up or cool down to the desired operating temperature of the temperature controlled zone. Once the unit is at operating temperature, it is loaded with a plurality of vials 98 holding any calibration samples and the substances to be analyzed, and the unit is ready to begin operation.

The carousel 150 and the vial delivery mechanism 160 are operated to begin delivering vials 98 into the temperature controlled zone 148 by transferring them into the passage. In the passage the vials 98 are in vertically aligned relation. Once in the temperature controlled zone the heating or cooling therein quickly causes headspace volumes in the vials to reach equilibrium with a liquid sample portion (or solid sample portion when the sample goes directly from a solid to a vapor phase). The achievement of equilibrium is facilitated not only by the rotation of the vials which is caused by the movement of the carousel, but is greatly enhanced by rotation of the vials in the passage by rotating device 106. The rotation of the vial causes a film of the substance to be present on virtually the entire inner cylindrical surface of the sample vial bounding the headspace. This film on the interior surface of the vial greatly increases the surface area from which the sample material evaporates into the headspace. The film is replenished with each rotation. As a result equilibration of the vapor phase and the non-vapor phase is rapidly achieved.

Once a vial in the passage moves adjacent flow needle 108, the actuator 114 moves the flow needle forward to pierce through the septum bounding the headspace of the vial. The six port valve 112 is initially in position to deliver pressurization flow of inert gas into the headspace 100 of the vial being sampled. This flow is continued until the pressurization flow observed by the operator at flow meter 124, or preferably as electrically sensed, reaches zero.

Once the vial is fully pressurized to the desired pressure, six port valve 112 changes its condition so that the headspace 100 is in fluid connection with the inlet of the gas chromatograph through port 114. Thereafter, valve 112 returns to its first condition as shown in FIG. 3 that the carrier gas is delivered through the flow conduit in the six port valve that was previously connected to the headspace. As a result, the sample, including the material in the flow conduit in the six port valve, is washed into the inlet of the gas chromatograph.

Once the sample is taken, the flow needle withdraws from the vial and the ejection plunger 148 retracts from the position shown in FIG. 3. This enables the vial 98 at the sample position to fall downward. The ejection plunger then moves forward to eject the vial from the machine through opening 158. At the same time, the vial immediately above in the passage is ready for sampling. The process is repeated as the delivery mechanism continues to deliver additional vials into the passage for sampling.

An advantage of one preferred embodiment of the present invention is that in the gas injection mode, if the gas flow at flow meter 124 does not reach zero, it is known that there is a leak and the results will be unreliable. Likewise, if the flow at flow meter 136 should fall to zero during the time that it is operable to wash the sample into the inlet of the gas chromatograph, it is known that there is a problem. These conditions may be signaled by use of an alarm or may be recorded by the controller and correlated with the particular sample vial, so that the results are questioned.

In certain environments where the column pressure of a gas chromatograph is high, the operating cycle of the apparatus of the present invention may include the opening of pressure release valve 138 prior to delivery of a sample to the gas chromatograph. The opening of the pressure release valve 138 will relieve the pressure on the column and will enable the sample to flow into the inlet of the gas chromatograph at lower pressures. The flow meter 136 also enables setting the flow so that the sample is delivered for analysis at the desired speed.

An alternative mode of operation for the preferred embodiment of the headspace autosampling apparatus is to control the pressurization of the headspace in accordance with pressure sensed at sensor 126. The pressurization of the vials to a uniform pressure rather than to a zero flow condition has the advantage of reducing the effects of the volatility of the materials in the sample matrix. Such approach also avoids conditions of too short pressurization time which may cause inadequate volume samples, or too long pressurization time which may result in diffusion of the vapor out of the headspace.

The method of control of the apparatus by pressurization of the headspace to a uniform pressure also enables identification of fault conditions. This is because a problem is immediately detected if the desired pressure is not achieved. As a result, it is known that any sample produced from the headspace of the corresponding vial is not meaningful data and should be disregarded.

The invention is also enabled to conduct multiple headspace extraction analysis by modifying the operating cycle of the apparatus. In multiple headspace analysis the headspace volume of the same sample is sampled by repeated withdrawal of material. By extrapolating from the decreasing concentration of the substance of interest, the original concentration of the material may be estimated. The repeated withdrawal of material from the headspace volume of a sample is accomplished by valve 172 and trap 174 shown in FIG. 3, operating the apparatus under control of a control program for this procedure in the processor.

The invention may be preferably operated in accordance with the analytical method known as the full evaporation technique (FET). Using FET headspace analysis matrix effects in samples are reduced. FET involves reducing the sample size and correspondingly controlling sample temperatures so that analyses are transferred completely from a condensed matrix to a confined vapor phase. This effectively eliminates the effect of the partition coefficient for the matrix. The technique is described in detail in the paper entitled "Matrix Independent Headspace Gas Chromatographic Analysis—The Full Evaporation Technique". Analytica Chimica Alta, 276 (1993) 235–245, Elsevier Science Publishers B.V., Amsterdam, authored by Dr. Michael Markelov and John P. Guzowski, Jr.

The preferred embodiment of the present invention is particularly well adapted for operation using FET autosampling. The use of the horizontally oriented sample vials as well as the film effect achieved by rotation of the vials about their longitudinal axis prior to sampling is particularly advantageous in achieving near complete vaporization of the substances of interest. Further, the careful temperature control of the pressurization gas and the sample assure reliable delivery of the sample to an analytical instrument.

Alternative approaches to extraction of the headspace of the vial may be used in alternative embodiments. Such approaches may include sweeping material from the headspace. This may be accomplished using a sample needle or functionally comparable device which displaces the headspace vapor by introduction of an inert gas through a first passage, and which causes the headspace vapor to flow through an outlet passage. The sample material swept from the headspace may be directed to an analytical instrument for analysis, or concentrated in a trap prior to analysis. Other approaches to extracting the headspace vapor may also be used.

Figure 10:
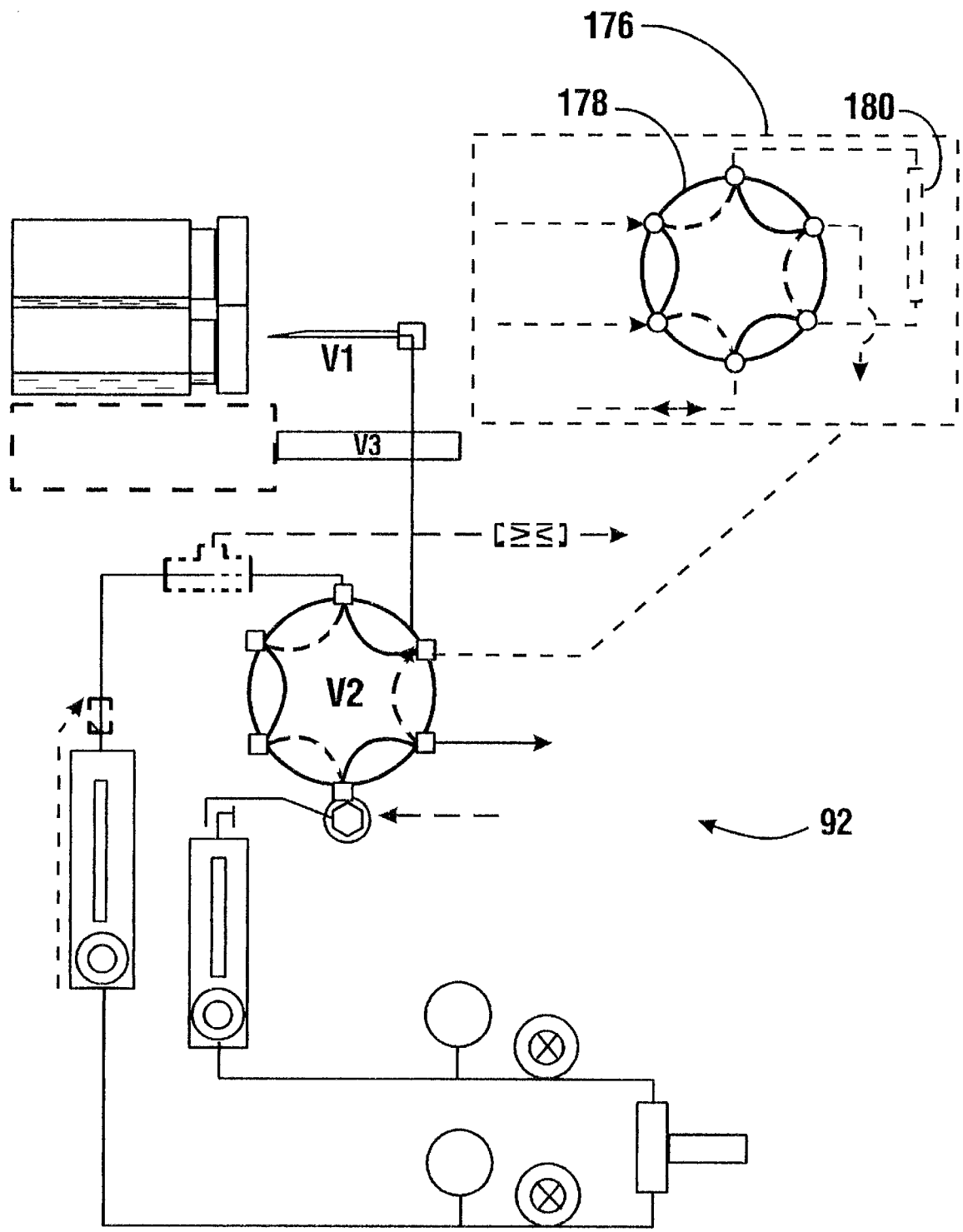
FIG. 10 is a schematic view of an alternative plumbing arrangement of the headspace sampling apparatus which includes a trap.

An alternative configuration of apparatus 92 may include a trap option as shown in FIG. 10. This alternative configuration includes an alternative connection arrangement 176 for the six port valve 178. In this alternative arrangement, a sample vial is pressurized in the manner previously described while carrier gas flows through a trap 180 to the gas chromatograph as shown in the valve position of FIG. 10.

When the condition of the six port valve 178 changes from that shown in FIG. 10, the sample passes through trap 180, and the material which is not captured in the trap passes to the gas chromatograph. Thereafter, the valve condition is returned to that shown in FIG. 10, and the material in the trap is selectively delivered for analysis, such as through heating of the trap.

The apparatus of the present invention is readily adapted to use the alternative arrangement 176 from the arrangement shown in FIG. 3. This gives the instrument of the invention enhanced flexibility and greater value.

Figure 11:
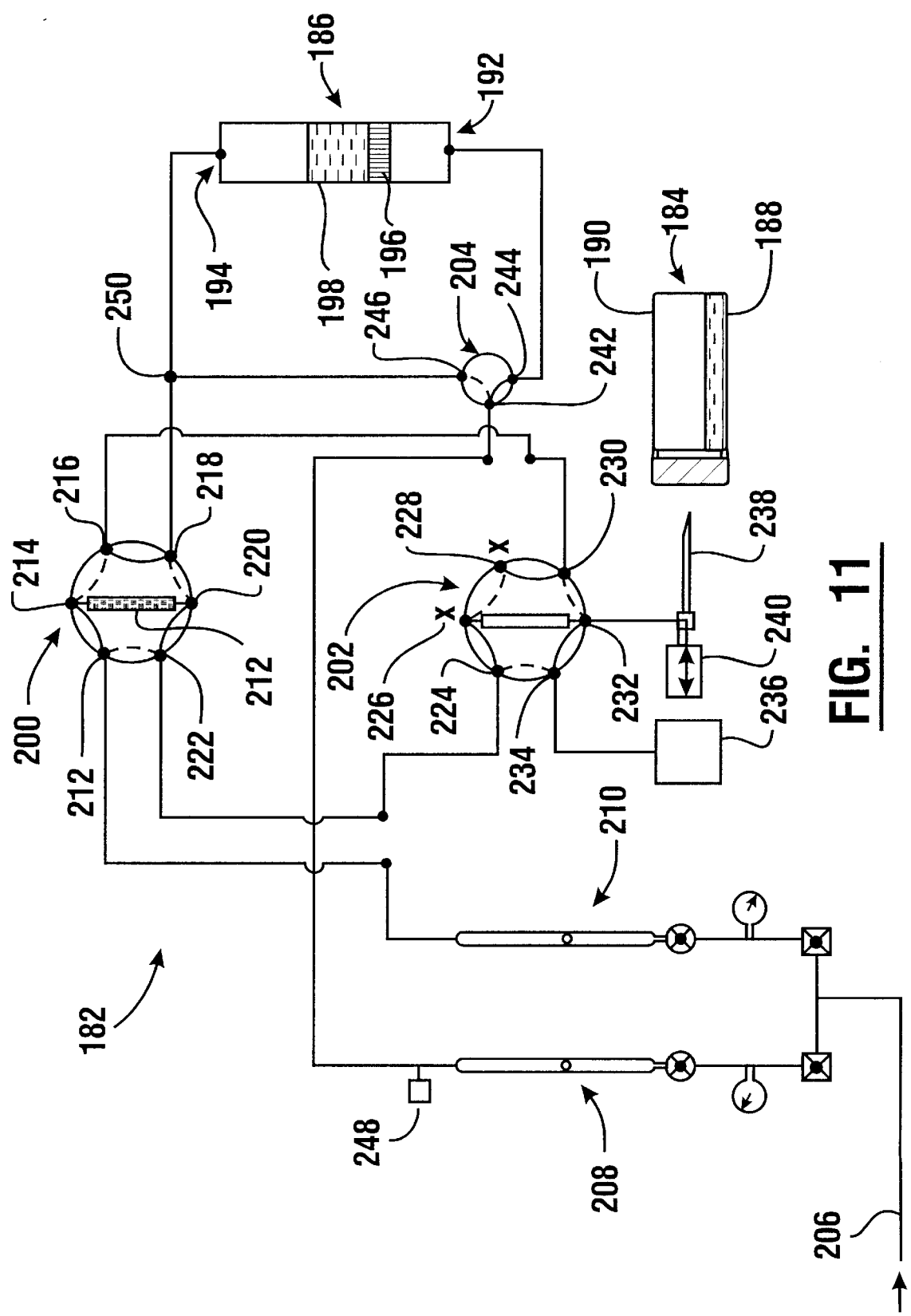
FIG. 11 is a schematic view of an alternative arrangement of the headspace sampling apparatus which can be used to perform purge and trap analysis on samples.

A further alternative embodiment of the system comprising a combined purge and trap and a headspace sampling unit 182 is shown in FIG. 11. The unit 182 is shown with both a vial 184 and a purge vessel 186. The vial 184 may be any of a conventional or unconventional type vial and is shown housing an enclosed substance. The substance equilibrates into a liquid and/or solid phase 188 shown at the bottom of the vial, and a vapor phase 190 shown in the headspace of the vial.

The purge vessel comprises a glass tube shown with both an inlet 192 and an outlet 194 connected to tubing. The vessel further preferably comprises a glass frit 196 disposed medially in the interior of the vessel between the inlet and the outlet. The glass frit includes a plurality of openings sized so that gas can pass through them but liquid is retained on the frit. A sample 198 is shown thus retained.

The unit 182 further comprises two six way valves 200 and 202, and a three way solenoid valve 204. All of these valves are automatically actuated between their two positions and act to route the gas flow through the unit. An inert gas is supplied to the unit at inlet 206. The inert gas flows to both a pressurization gas pathway 208 and a carrier gas pathway 210. These gas pathways preferably include instrumentation which can both indicate and control the flow and pressure of the gas flowing through each pathway.

The unit 182 also includes a trap 212, which is connected across ports 214 and 220 of valve 200. This trap comprises a tube through which gas can flow. The tube encloses a porous material suitable to adsorb the VOC or other compound being tested, and desorb the same VOC or compound when the adsorbent is heated.

The unit 182 fluidly communicates with a gas chromatograph 236 or other analytical instrument via port 234 of valve 202. The valve 202 also communicates with a needle 238. The sample needle is automatically moved into and out of the vial 184 by actuating rod 240. When retracted from the vial the sample needle can act as a vent for gas to flow to the atmosphere. In the embodiment shown ports 226 and 228 of valve 202 are plugged.

The gas flowing from the pressurization pathway 208 is routed to port 242 of the three way solenoid valve 204. When the valve is in the position represented with dashed line the gas is routed to the trap 212. When the valve is positioned represented by the solid marked line the gas in the pressurization pathway flows to the purge vessel 186.

In operation the unit is initially positioned in a standby mode. In this standby mode the flow paths represented by dashed lines of valves 200, 202 and 204 are open enabling flow therethrough, and the needle is retracted from the vial. The gas from the pressurization pathway 208 flows to port 218 of valve 200 via port 246 of valve 204. The gas sweeps across the trap 212 and flows out to the atmosphere via ports 214 and 216 of valve 200, port 230 and 232 of valve 202 and the needle 238. In standby mode the carrier gas flows from the carrier gas pathway 210 to the gas chromatograph 236 via port 212 and 222 of valve 200 and ports 224 and 234 of valve 202.

When a purge and trap operation is to be performed, a sample is introduced onto the frit 196 of the purge vessel 186. To put the unit into purge mode the valve 204 is positioned so that the flow path shown as solid lines is open. Both of the valves 200 and 202 remain in the position with the flow paths shown as dashed lines open. The needle 238 remains retracted from the vial 184. In the purge mode gas flows from the pressurization pathway 208 to the purge vessel via ports 242 and 244 of valve 204. The gas passes through the many passages through the frit 196 and bubbles up through the sample 198. A gas flowrate through the frit is preferably maintained so that the gas does not jet or form large expanding bubbles. Instead a large number of relatively small bubbles are preferably formed by the gas, which flow separately from the frit through the liquid sample 198 to the liquid gas interface of the sample and the headspace of the purge vessel. The plurality of bubbles in aggregate comprise a large liquid gas surface area. This large surface area acts to increase the mass transfer rate of the volatile molecular components of the sample 198 from the liquid phase to the vapor phase. The agitation of the liquid sample by the gas bubbles also acts to increase this mass transfer to the gas phase.

The volatilized components are then convectively transferred out of the purge vessel and to the trap 212 via ports 218 and 220 of valve 200. The volatilized components of the sample are adsorbed onto the media contained within the trap as the gas flow passes through the trap. The gas thus stripped of the volatilized components of the sample flows to the atmosphere via ports 214 and 216 of valve 200, ports 230 and 232 of valve 202 and the needle 238.

The purge mode is operated on a timed basis. The purge mode flowpath is maintained for a preset period of time which is sufficient to fully volatilize the desired components from the sample contained in the purge vessel. This preset time is preferably stored in the memory of the programmable controller. The preset times can be programmed for purposes of purging different types of samples.

After the purge mode time period is counted down by the controller the controller causes the unit to either enter a dry purge mode or a desorbing mode. The dry purge mode is used to rid the trap of excess water which was convectively transferred from the purge vessel 186 and was accumulated in the trap 212. In this dry purge mode the three way solenoid valve 204 is returned to the position it occupied in the standby mode where the port communicated along the flow path represented by dashed lines. The gas is thus routed from the pressurization gas pathway 208 to the trap via ports 242 and 246 of valve 204, and ports 218 and 220 of valve 200. The gas sweeps the trap of accumulated water and carries it out of the unit via ports 214 and 216 of valve 200, ports 230 and 232 of valve 202 and the needle 238. The sweeping gas flow across the trap is maintained for a desired preset time period. The sweeping gas flow does not affect the adsorbed chemicals on the adsorbent within the trap.

If the dry purge mode is not required or desired, the unit immediately enters into the desorb mode after the termination of the purge mode. Alternatively if the dry purge mode is utilized, the unit switches to the desorb mode after the dry purge mode. In the desorb mode the unit occludes the trap from the rest of the unit and then heats the trap. The trap is occluded by first moving the needle 238 to a closed environment. This closed environment can take the form of a vial such as vial 184 or a special block composed of an elastic medium that blocks the exit of the gas from the needle. The occlusion operation can be monitored and controlled by the flow measurement device included in the pressurization gas tram 208. When the flow of gas through the pressurization train is stopped, the flow measurement device communicates to the controller that the trap is occluded. Once the signal is received by the controller, the controller initiates the heating of the trap. The occlusion operation can alternatively be monitored by pressure transmitter 248 which sends a signal to the controller corresponding to the pressure in any of the lines downstream of the pressurization gas train. The controller compares the pressure to that of the pressure signal received from the pressure transmitter in the pressurization gas train. When the two pressures are equal the controller initiates the heating of the trap.

In the heating operation the trap temperature is increased to a desorption temperature appropriate to desorb the previously absorbed chemicals from the material which is used in the trap. These temperatures are often specified in published purge and trap procedures. The desorbed chemicals reenter the gas stream. Because of the stagnant gas surrounding the trap the desorbed chemicals remain in the vicinity of the trap. The heating operation time is also a preset value which is resident in memory and counted down by the controller. At the end of the heating operation the unit switches from a desorb mode to an inject mode.

In the inject mode the valve 200 is modulated so that the flow paths represented by solid lines are open. The pressurization gas remains stagnant in the inject mode as the needle remains in a closed environment. During the previous standby, purge, dry purge, and desorb modes the gas flowing from the carrier gas train 210 has been flowing to the gas chromatograph via ports 212 and 222 of valve 200, and ports 224 and 234 of valve 202. Because of the port flow changes in valve 200 the gas flowing from the carrier gas train is routed through the trap 212 via ports 212 and 214. The carrier gas sweeps the desorbed gasses from the trap and convectively transfers it to the gas chromatograph via ports 220 and 222 of valve 200, and ports 224 and 234 of valve 202.

The purge and trap operation can alternatively be performed automatically on a plurality of samples using a plurality of purge vessels. Each of the purge vessels comprise a tube with a medially disposed frit. The gas inlet of each purge vessel is operatively fluidly connected with port 244 of valve 204. The inlets can be connected via a multiplexing valve which directs the flow of gas from port 244 of valve 214 to a first purge vessel. The outlets of all of these purge vessels are fluidly connected to point 250 on the tubing. Thus connected the purge and trap operation is conducted on a first purge vessel. Once the purge and trap operation is completed the multiplexing valve automatically is switched to connect port 244 of valve 204 to an adjacent or second purge vessel. The purge and trap operation is then automatically performed by the unit on this second purge vessel. When a particular purge vessel is connected to the port 244 of valve 204 the other purge vessels are isolated from the gas flows within the unit, therefore the enclosed samples in these purge vessels are not contaminated by any other samples. Thus any number of sample containing purge vessels can be automatically analyzed.

Figure 12:
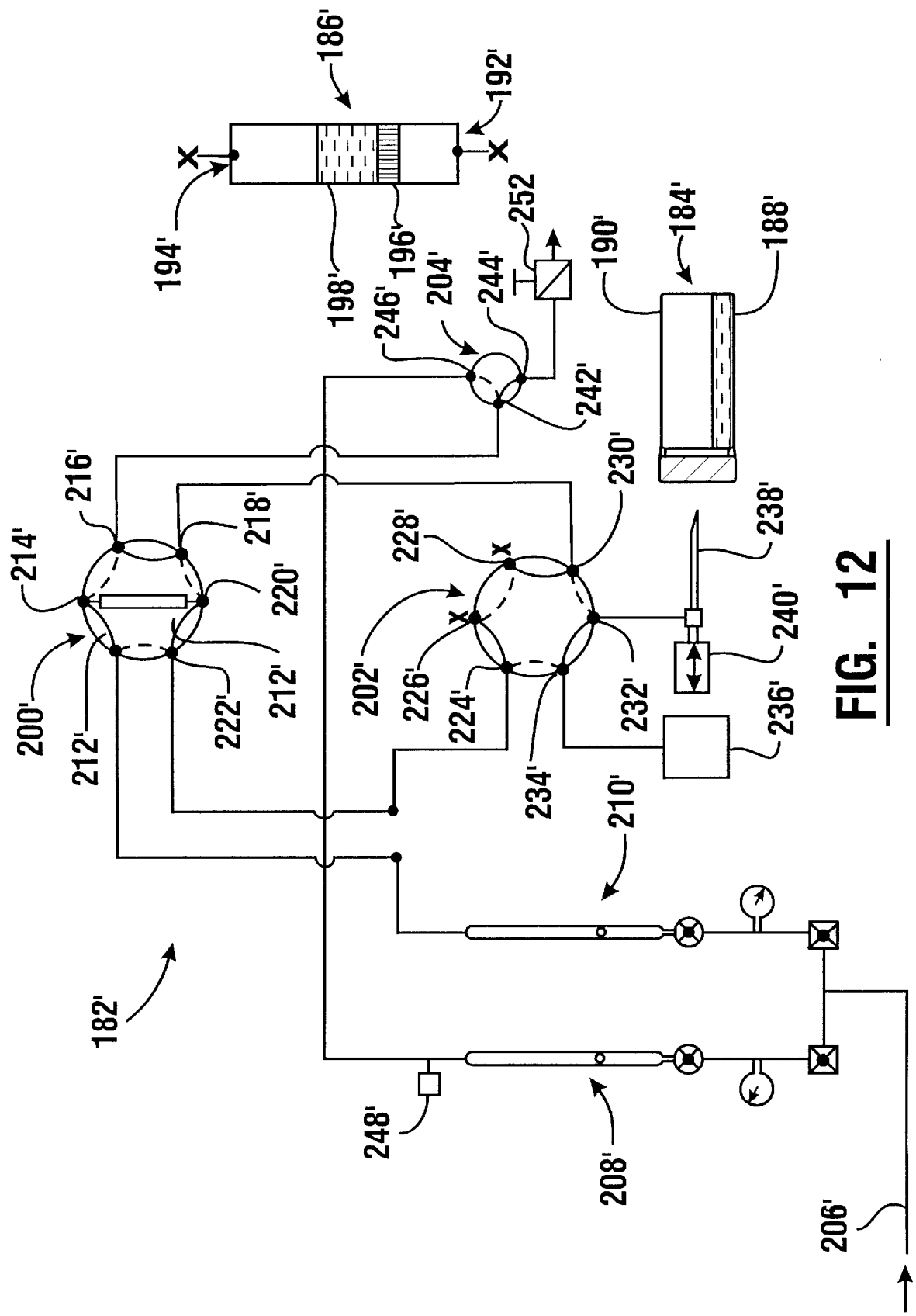
FIG. 12 is a schematic view of an alternative plumbing arrangement of the apparatus depicted in FIG. 11.

In addition to the purge and trap operation the combined purge and trap and headspace analysis unit shown in FIGS. 11 and 12 can be used to perform: direct headspace analysis of sample vials using a time controlled injection; direct headspace analysis of sample vials using a volume control injection; headspace analysis of vials using a trapping preconcentrator; and high sensitivity FET on sample vials.

The direct headspace analysis of samples can be performed by the unit 182 in the configuration shown in FIG. 11. The purge vessel is emptied or plugged if a sample is contained therein. Initially valves 200, 202 and 204 are positioned so that the dashed flow paths are open. Initially the needle is retracted from the vial, and the vial with contained sample is heated in the previously described heating zone. Gas from the pressurization gas pathway 208 flows through the retracted needle to the atmosphere sweeping any contaminants from the tubing. The gas from the carrier pathway 210 similarly sweeps the column within the gas chromatograph.

After a time is allowed for the lines to be swept and the sample to be heated long enough so that the enclosed sample has reached an equilibrated state, the vial headspace is pressurized. The needle 238 is first plunged into the headspace 90 through the septum of the vial 184 by the actuating rod 240. The gas flowing from the pressurization pathway 208 is then injected into the headspace of the vial on a time controlled or volume controlled basis. In a time controlled injection the gas is allowed to flow into the headspace for a preset time. The headspace pressure steadily increases throughout the injection period. The flow meter in the pressurization gas pathway can be used to measure the gas flowrate entering the vial in the injection period. These sensed flowrates can then be used by the controller to determine and record the total volume of gas injected into the vial. At the end of this injection time period the valve 202 is switched by the controller so that the flow paths represented by solid lines are open. When this occurs the pressurized headspace acts as the gas source for the column of the gas chromatograph 236. The gas flows from the headspace through the sample needle to the gas chromatograph via ports 232 and 234 of valve 202. The gas from the carrier pathway is stopped by the occluded port 226. The gas is allowed to vent from the headspace to the gas chromatograph for a preset period of time. At the end of this time the valve 202 is switched back to the position it occupied during the standby mode, and the needle is retracted from the vial headspace. The vial can then be ejected and the procedure performed on the next vial.

The vial can alternatively be injected with gas at a preset pressure. The gas is injected until the pressure transducer contained within the pressurization gas pathway reaches a preset value. The gas pressure in the headspace continually increases until the time when the controller senses the preset pressure has been reached and actuates the valve 202 to move to the position in which the gas flow paths represented by solid lines are open. At this time the gas from the headspace is vented to the column of the gas chromatograph.

The unit 182 may have an alternative configuration shown in FIG. 12. In FIG. 12 the components of the unit are substantially similar to those in FIG. 11, and the similar components are indicated by prime numerals to distinguish them for purposes of comparison of the two configurations of the unit. In the unit 182' the purge vessel 186' is isolated from the unit by having both its inlet 192' and its outlet 194' plugged or occluded. The tubing configuration of unit 182' differs from that of unit 182 in that port 218' of valve 200' is connected to port 230' of valve 202'. Port 216' of valve 200' is connected to port 242' of valve 204' and the pressurization gas train 208' is connected to port 246' of valve 204'. Unit 182' also includes a vent valve which is preferably simply an automatic on/off valve 252. The vent valve allows port 244' of valve 204' to selectively communicate with the atmosphere. The vent valve 252 is normally open.

The unit 182' can be used to perform headspace analysis of samples using the trap 212' in a reconcentration mode. In this procedure the unit is initially in a standby mode in which the valves 200', 202' and 204' are positioned so that the flow paths represented by dashed lines are open. In this standby mode the needle 238' is retracted from the vial 184' and gas from the pressurization pathway 208' sweeps the gas lines and the trap 212' through the retracted needle, while gas from the carrier gas train 210' sweeps the column of the gas chromatograph 236'. While the unit is in standby mode the vial 184' is heated and rotated as described above in the same way as the vials are treated in the standby modes associated with unit 182.

When the sample in the vial 184' has reached equilibrium, the unit 182' enters a headspace pressure mode. The controller causes actuating rod 240' to plunge the needle 238' into the vial 184' and the headspace of the vial is pressurized from gas from the pressurization pathway 208'. The pressurization of the vial can be done on a time controlled basis or a pressure or flow controlled basis as described above. After the headspace has been pressurized the unit 182' enters the purge mode.

In the purge mode the controller switches the position of valve 204' so that the trap is vented to atmosphere via ports 214' and 216' of valve 200', ports 242' and 244' of valve 204' and the vent valve 252. When valve 204' is in this position the headspace of vial 184' is allowed to depressurize to atmosphere through the trap 212'. The volatilized sample components are absorbed onto the material contained within the trap 212' and the remaining gasses flow to the atmosphere. This purge mode is preferably continued for a preset time by the controller, and at the end of the time period the trap is occluded and heated in a desorption mode. The controller can alternatively put the unit 182' into a dry purge mode in which dry gas from the pressurization train sweeps the trap to remove any accumulated water.

At the start of the desorption mode the controller switches the valve 204' back to the initial position in which port 242' communicates with port 244'. The controller also closes the vent valve 252. The gas flow from the pressurization pathway is thus halted and the trap is surrounded by a stagnant gas. The controller then causes the heating of the trap. The trap 212' is heated for a preset time sufficient to revolatize the adsorbed gasses of the sample. After this time the controller puts the unit 182' into an injection mode.

In the injection mode the valve 200' is positioned so that the flow paths shown as solid lines are open, the valve 242' and valve 202' remain in their previous positions. The gas from the pressurization pathway 210' now sweeps the trap of the desorbed gasses by flowing to the trap via ports 212' and 214' of valve 200'. The gas then convectively transfers the desorbed gasses to the gas chromatograph 236' via ports 220' and 222' of valve 200' and ports 224' and 234' of valve 202'. The sampling thus completed, the vial is ejected and the analysis cycle on the next vial is initiated.

The alternative configuration of the unit 182' can also be used for simple headspace analysis in the above described manner without utilizing the trap to reconcentrate the volatilized components of the sample. Both of the units 182 and 182' can be used to perform FET analysis, in which the sample size is reduced and headspace analysis is performed on the fully volatilized components of the sample.

Although the preferred embodiment of the headspace autosampling apparatus of the present invention employs a carousel for holding sample vials, other embodiments of the invention may employ other types of holding devices. For example, the invention may be operated with a magazine type tower for holding a single stack of sample vials. Other embodiments may use other types of bins or feeding mechanisms.

A further advantage of preferred embodiments of the present invention is that it is very compact and may be mounted directly on a gas chromatograph or other analytical instrument. This avoids the need for long transfer lines and the possible inaccuracies which may result due to condensation of the sample material in such lines.

One preferred embodiment of the invention is also equipped with a manual injection port. This port is particularly advantageous in that it is mounted on the six port valve, and manually injected samples travel by the same route as those taken automatically. As a result, the present invention may be operated by direct syringe sampling techniques without disconnecting the apparatus from the gas chromatograph, and the sensitivity is maintained for both sample types.

The preferred form of the headspace autosampling apparatus of the present invention achieves several fundamental advantages over the prior art as a result of sampling the headspace in cylindrical vials that are oriented so that their longitudinal axes extend in a generally horizontal direction. In this orientation, the surface area of evaporation for the substance to be analyzed is substantially increased from normal vials which are sampled with a longitudinal axis in a generally upright condition. The increase in surface area significantly decreases the time required to reach equilibrium between the non-vapor phase substance and the vapor phase of the substance in the headspace.

A further advantage of the orientation and configuration of the vials of certain preferred embodiments of the headspace sampling apparatus of the present invention is that the thickness of the liquid layer of a substance to be analyzed is reduced. This reduction in thickness results in a dramatic increase in diffusion rate of a component to the liquid/gas interface, because diffusion time is a square function of the thickness of the substance layer.

The horizontal position of the vials also facilitates their rotation while in the temperature controlled zone. As a result of rotation, liquid or solid samples may form a thin film on the interior walls of the vials. This greater surface area and decreased thickness of the film further increase the rate of diffusion of the sample into the headspace and reduce the time for the non-vapor phase of the substance to achieve equilibrium with the vapor phase in headspace. The film is also replenished with each rotation further speeding achievement of equilibrium. Optimally the vials are rotated a plurality of times prior to sampling. Heat transfer to the sample is also facilitated. Applicant has found that cylindrical vials in which the length is 1.6 times the radius are well suited for this purpose. However, other embodiments may use vials having other configurations.

A further advantage of the rotation of the vessels containing the substances for analysis is that rotation helps to increase the heat transfer to or from the substance in the vial. The thin film of liquid clings to the interior surface glass vial and readily absorbs heat through the vial wall. The lower boiling components of the liquid volatilize with this heat increase. With the continued rotation of the vial the adhering volatilized components are reintroduced back into the bulk liquid portion of the sample. This reflux acts to increase the separation of the volatile components from the rest of the sample.

The generally horizontal orientation of the sample vials also enables certain preferred embodiments of the present invention to be much more compact and to hold a large number of samples in a machine that occupies very little space.

A further significant advantage of the present invention is that the vials used in certain embodiments include a novel twist off cap and septum construction. Prior art headspace sample vials have used a cover that is crimped over the vertically oriented opening. Crimping is undesirable because it makes reopening and reclosing vials difficult. This can be a problem where it is desired to add materials to the vial after initial closure.

A further fundamental advantage of the vials that are a part of the present invention is that they are well suited for handling by robots. This reduces labor costs and facilitates sample preparation of materials that pose risks in manual handling.

One preferred form of the vials of the invention achieves the desired results by using temperature resistant caps comprised of phenolic plastic and a silicone rubber septum for sealing between the vial and the cap. The septum is generally TFE coated on its interior surface, but other coatings such as metallic coatings may be used depending on the type of sample.

Figure 13:
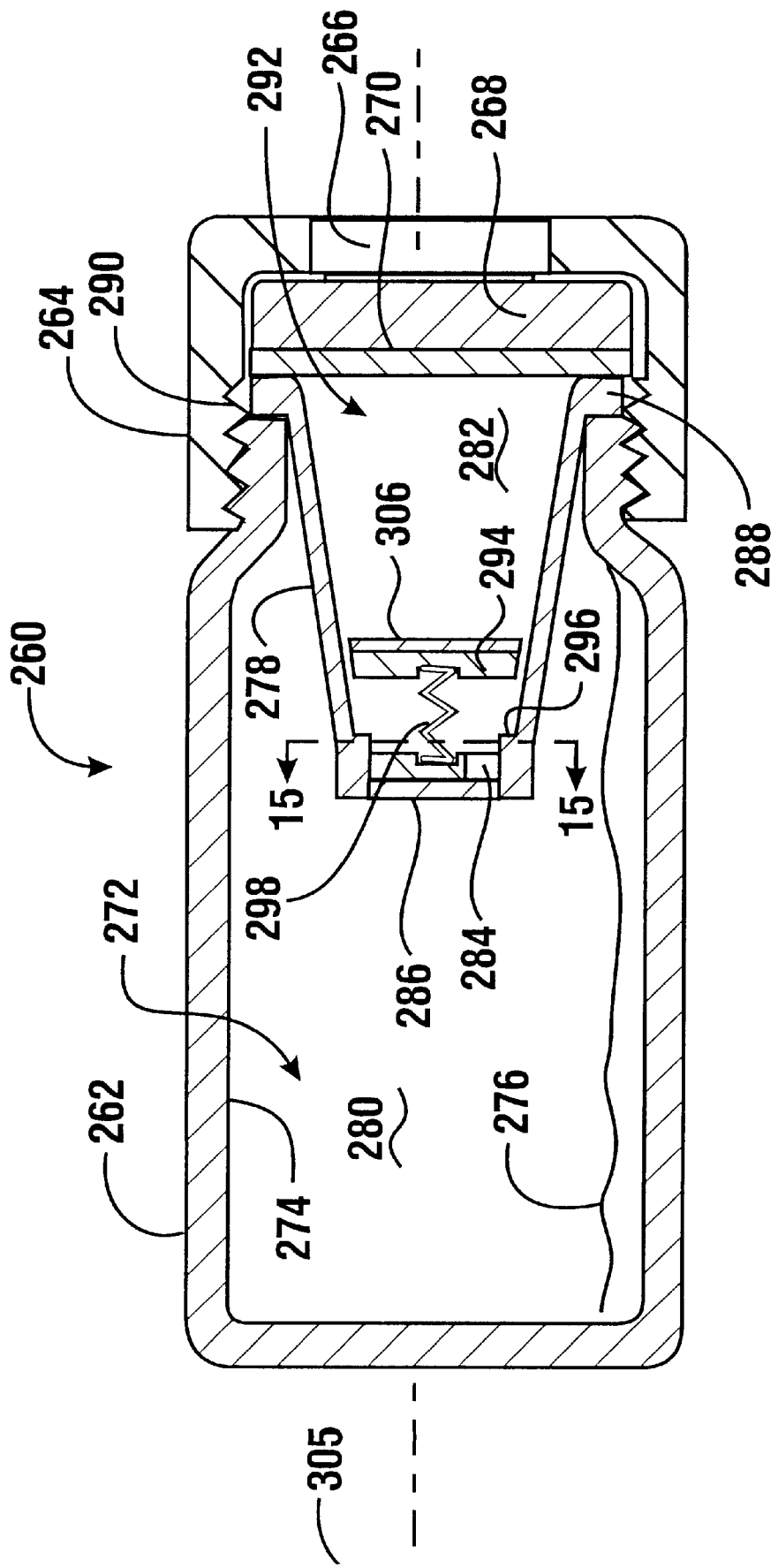
FIG. 13 is a cross sectional view of an alternative form of a vial used in connection with the headspace autosampling apparatus, showing an internal valve mechanism in an open condition.
Figure 15:
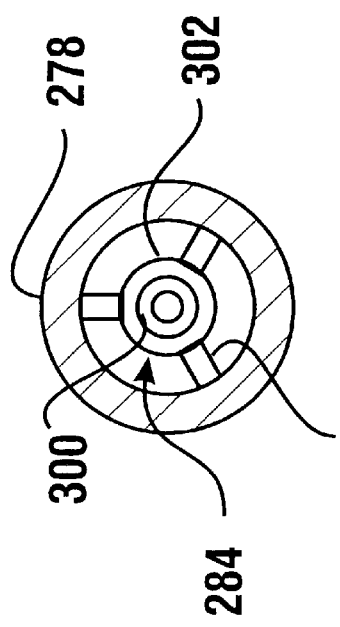
FIG. 15 is a sectional view of a dividing member in the vial taken along line 15—15 in FIG. 14.
Figure 14:
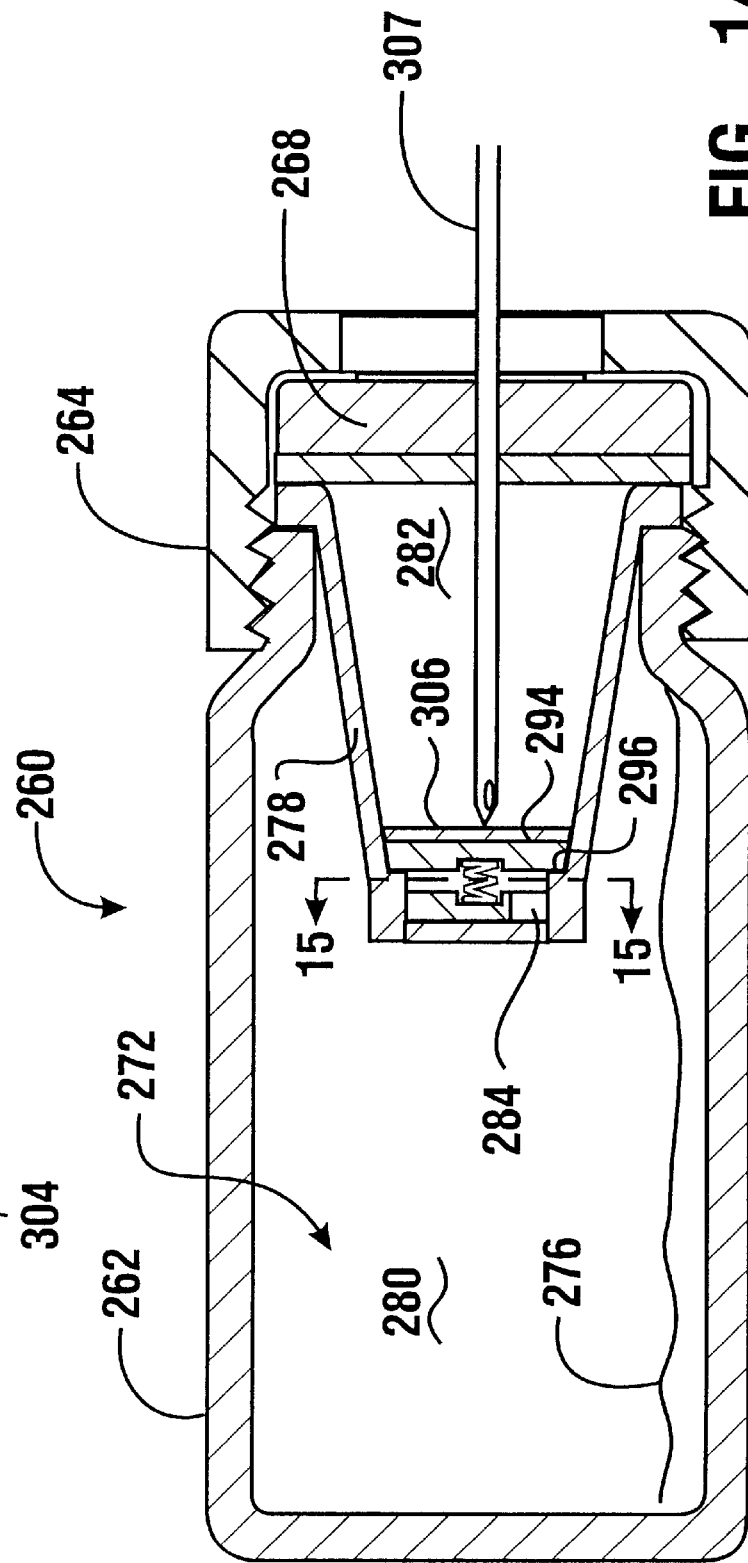
FIG. 14 is a view of the alternative form of the vial shown in FIG. 13 with the valve mechanism in a closed condition.

An alternative form of a container or vial generally indicated 260 used in connection with a headspace sampler is shown in FIGS. 13 through 15. Vial 260 is generally similar to vials 98 previously described and provides the advantages discussed in connection therewith. In addition, vial 260 is configured to minimize the effects of extracting a sample from the vial on the concentration of the constituents in the extracted sample.

Vial 260 includes a generally cylindrical vial body 262. A cap 264 is releasibly engaged to the vial body by cooperating threads that extend on the cap and vial body. Cap 264 includes an aperture 266. Aperture 266 overlies a penetrable septum 268. Septum 268 is similar to the septums used in the vials previously described and includes a layer 270 on its interior surface comprised of a plastic or metallic material. The composition of the layer 270 on the septum may be varied depending on the nature of the substance to be held within a vial.

The body 262 and cap 264 bound an interior area of the vial generally indicated 272. Interior area 272 is bounded within the vial by an interior surface 274. Interior surface 274 is a generally cylindrical surface. The interior surface 274 supports a non-vapor phase of a substance for analysis generally indicated 276.

A dividing member 278 extends in the interior area 272 of the vial. Dividing member 278 is a generally conical member and divides the interior area of the vial into a first portion generally indicated 280 and a second portion 282. The dividing member includes at least one opening 284. Opening 284 is adjacent a tip of the dividing member and serves as a fluid passage which enables fluid to communicate between the first portion 280 and the second portion 282. A screen 286 overlies the opening in the embodiment shown. Screen 286 restricts the passage of fluids other than vapor through the opening.

At an end opposed from opening 284 the dividing member 278 includes an annular flange portion 288. Flange portion 288 extends generally radially outward from the dividing member. In the assembled condition of the vial 260 the flange portion is held in intermediate relation between an annular lip 290 which bounds an opening 292 of the vial body and the septum 268 underlying the cap 264. As can be appreciated from FIGS. 13 and 14, this construction enables the dividing member 278 to be readily inserted and removed from the interior area of the vial when the cap 264 is disconnected from the vial. As a result, the substance to be analyzed 276 may be introduced into the interior area of the vial prior to the dividing member, septum and cap being engaged to the vial body. The interior area 272 is then sealed after the substance is introduced by installing the dividing member through the opening 292 and then attaching the septum and cap. Once the cap is installed the vapor and non-vapor phase of the substance 276 are enabled to equilibrate within the interior area 272 in the manner previously described.

A useful aspect of vial 260 is that it includes a valve mechanism which controls flow through the fluid passage in the dividing member that separates the first and second portions of the interior area of the vial. In the embodiment shown the valve mechanism includes a movable closing member 294. Closing member 294 is sized to be movable within the interior of the conical dividing member and has a diameter sized so that fluid may flow past the closing member when the closing member is in the position shown in FIG. 13.

Closing member 294 is sized sufficiently large so that it can engage an internal annular lip 296 on the dividing member in generally fluid tight relation as shown in FIG. 14. When the closing member is in abutting engagement with the lip 296, flow through the opening 284 is generally prevented and the first portion 280 in the vial which holds the substance 276 is generally isolated from the vapor in the second portion 282 of the vial.

Closing member 294 in the embodiment shown is biased toward a position opening flow through opening 284 by a spring 298. Spring 298 is preferably supported in a central recess of the closing member and is held thereto in engaged relation by a detent or similar structure. The end of the spring opposite the closing member is held in a recess 300 in a central support area 302 of the dividing member as shown in FIG. 15. The central support area 302 is supported by projections 304 which extend in opening 284. This configuration provides support for the spring while enabling fluid flow through the opening.

It should be understood that the spring is attached within the recess 300 by a detent or functionally similar means to prevent it from disengaging from the support area 302. Spring 298 is preferably a spring which has a sufficiently strong spring rate to reliably enable closing member 294 to move between the positions opening and closing the fluid passage through the dividing member.

The dividing member 278, screen 286, spring 298 and closing member 294 are preferably comprised of materials that are compatible with the substances to be analyzed in the interior area of the vial. In embodiments of the invention, the closing member 294 may be comprised of layers of material which are adapted for use in connection with the particular application. In the embodiment shown in FIGS. 13 and 14, the closing member includes an outer layer 306 that is designed to resist penetration and protect an underlying layer which may be a material of lesser hardness, or a resilient material.

In operation of the invention using the alternative sample vial 260, the substance 276 is placed in the interior area of the vial through the opening 292. Thereafter the dividing member 278 is installed in abutting relation with the lip 290 of the vial. Thereafter the penetrable septum 268 is installed in overlying relation of the opening and the dividing member. Thereafter the cap 264 is threadably secured to the body of the vial such that the interior area is generally fluid tight.

Once the vial 260 is assembled with the substance 276 held therein the vial may be rotated about a central axis schematically indicated 305. In a preferred form of the invention the vial may be rotated with the central axis 305 extending generally horizontally in the manner of the previously discussed embodiments. When the vial is rotated in this manner the interior surface 274 of the vial is coated with a film of the substance so as to speed achieving equilibrium within the interior area of the vial. In addition, it should be noted that because the opening 284 in the dividing member is disposed away from the interior surface of the vial, the risk of the non-vapor phase of the substance 276 passing through the opening 284 is minimized.

It should be understood however that while in the preferred embodiment vial 260 is used in a horizontal position.

In other embodiments the vial may be used with the central axis 305 extending in a generally vertical direction or in other directions. The nature of the vial 260 is such that it will provide benefits when used in connection with analytical instruments that do not prepare the samples with horizontal rotation.

As a result of heating (or in some cases cooling) through a rotation of the sample or by passage of time, the vapor and non-vapor phases of the substance 276 for analysis reach equilibrium within the interior area 272 inside the vial. The non-vapor phase of the substance extends in both the first portion 280 and the second portion 282 of the interior area. This is because the closing member 294 when it is in the position shown in FIG. 13 enables flow through the fluid passage in the dividing member.

As shown in FIG. 14, when the vapor phase is to be sampled a sample needle 307 is extended through the septum and into the second portion 282 of the interior area of the vial. As the sample needle is extended into the interior area it is operative to move closing member 294 to the position where it engages interior lip 296. This movement of the closing member to the closed position cuts off fluid flow through the opening 284 in the dividing member 278. The sample vapor may then be extracted from the second portion 282 while the second portion is isolated from the first portion 280 of the vial. Because first portion 280 houses the non-vapor phase of the substance 276 the amount of the substance in the vapor phase does not change during the sampling process. As represented in FIG. 14, the preferred form of the invention uses a sample needle which includes one or more side ports. This is done to prevent the engagement of the needle with the closing member 294 from restricting the passage of fluid into and out of the needle. The layer 306 on the closing member is preferably operative to protect the closing member from being damaged by engagement with the needle.

It will be appreciated that the alternative form of the vial 260 may be used with various modes of operation of the headspace autosampling apparatus of the present invention. Alternatively, the alternative vial 260 may be used with other types of sampling devices and analytical instruments to prevent changes in the amounts of constituents of the substance in the vapor phase of the sample concentration as the result of the sampling activity.

It should be understood that the particular configurations for the dividing member and valve mechanism present advantages when used in connection with the embodiments of the invention described herein. In other embodiments alternative constructions for the valve mechanism, the body member and other components may be used.

Thus, the new headspace autosampling and vial apparatus and method of the present invention achieve the above stated objectives, eliminate difficulties encountered in the use of prior devices and systems, solve problems and attains the desirable results described herein.

In the foregoing description certain terms have been used for brevity, clarity and understanding, however no unnecessary limitations are to be implied therefrom because such terms are for descriptive purposes and are intended to be broadly construed. Moreover, the descriptions and illustrations are by way of examples and the invention is not limited to the details shown and described.

Further in the following claims any feature described as a means for performing a function shall be construed to encompass any means capable of performing the recited function and shall not be deemed limited to the particular means used for performing the function in the foregoing description, or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations and relationships are set forth in the appended claims.

I claim:

1. A method for supplying a vapor phase sample to an analytical instrument comprising the steps of:
    a) placing a non-vapor phase of a substance for analysis in an interior area of a vial, wherein the interior area includes a first portion and second portion, wherein a dividing member fluidly separates the first portion from the second portion, and wherein a fluid passage extends through the dividing member between the first and second portions, and wherein the non-vapor phase of the substance is contained only in the first portion;
    b) generating a vapor phase of the substance in the interior area, wherein the vapor phase extends in both the first and second portions;
    c) closing the fluid passage with a closing member;
    d) removing a sample of the vapor phase from the second portion; and
    e) introducing the sample into an analytical instrument.

2. The method according to claim 1 wherein the vial includes an opening, and prior to step (c) further comprising the step of:
    f) extending the dividing member into the interior area through the opening.

3. The method according to claim 2 wherein subsequent to step (f) and prior to step (c) further comprising the step of:
    g) installing a penetrable septum in overlying relation of the opening.

4. The method according to claim 3 wherein subsequent to step (g) and prior to step (c) further comprising the steps of:
    h) installing a cap in engagement with the vial in overlying relation of the septum, wherein the cap holds the septum in overlying section of the opening.

5. The method according to claim 1 wherein the vial includes an interior surface, wherein the interior surface bounds the first portion, and prior to step (c) further comprising the step of:
    f) moving the vial to coat the interior surface with the non-vapor phase of the substance.

6. The method according to claim 5 wherein the vial comprises a generally cylindrical vial body having a central axis, and wherein step (f) comprises rotating the vial about the central axis.

7. The method according to claim 6 wherein in step (f) the vial is rotated with the central axis extending generally horizontally.

8. The method according to claim 1 wherein step (c) includes moving the closing member with a sample needle extending in the second portion of the interior area.

9. The method according to claim 8 wherein step (c) further includes moving the closing member with the sample needle against the opposing force of a biasing member, to a position blocking the fluid passage.

10. The method according to claim 1 wherein step (d) includes extracting vapor from the second portion through a fluid passage extending in a sample needle.

11. The method according to claim 1 wherein step (b) includes equilibrating the vapor phase and the non-vapor phase within the interior area of the vial.

12. The method according to claim 11 wherein step (b) further includes heating the substance in the interior area.

13. The method according to claim 12 wherein step (b) further includes moving the non-vapor phase of the substance relative to the vial within the first portion.

14. The method according to claim 1 wherein the vial comprises a container, wherein the container generally bounds the interior area, and wherein the container includes an opening therethrough to the interior area and wherein the closing member is movable relative to the container, wherein the closing member is movable between a closing position closing the fluid passage and an open position wherein fluid is enabled to flow through the fluid passage, and wherein in step (c) closing member is moved to the closing position and in step (d) the sample is removed through a penetrable septum, wherein the septum is in overlying generally fluid tight relation with the opening of the container.

15. The method according to claim 14 wherein the first portion of the interior area is generally bounded by an interior surface, and wherein the fluid passage terminates in the first portion at a first opening, and wherein during step (c) the first opening is disposed from the interior surface.

16. The method according to claim 15 wherein prior to step (c) further comprising the step of extending a sample needle through the septum, wherein in step (c) the sample needle operatively moves the closing member to the closing position, wherein the sample needle includes a needle passage, and wherein in step (d) the needle passage is in fluid communication with the second portion.

17. The method according claim 16 wherein the analytical instrument is in fluid communication with the needle passage in the sample needle.

18. The method according to claim 14 and prior to step (c) further comprising the step of biasing the closing member toward the open position with a biasing member, wherein the biasing member is in operative connection with the closing member.

19. The method according to claim 14 wherein the dividing member includes a generally conical member including a tip portion, and wherein the fluid passage extends through the dividing member adjacent the tip portion.

20. The method according to claim 11, wherein the conical member further includes an annular flange portion and pair to step (c) further comprising the step of extending the flange portion in intermediate relation between the septum and the container.

21. The method according to claim 19 wherein the container further comprises a cap, including an aperture and prior to step (b) further comprising the step of placing the cap in operative engagement with the container, wherein the septum extends in intermediate relation between the cap and the second portion, wherein the septum is accessible through the aperture.

22. The method according to claim 19 wherein the container comprises a generally cylindrical container body, wherein the container body has a central axis, and wherein the fluid passage adjacent the tip portion of the dividing member extends generally adjacent the central axis and prior to step (c) further comprising the step of coating an inside wall of the container body with the non-vapor phase of the substance by rotating the container body general about the axis.

23. The method according to claim 22 wherein step (c) includes moving the closing member to the closing position with a sample needle, wherein the sample needle is in operative connection with an actuator, wherein the actuator is operative to selectively move the needle through the septum, wherein when the needle is extended through the septum the needle is generally in alignment with the central axis and is operative to move the closing member to the closing position, wherein the needle includes a needle passage, and wherein when the needle is extended through the septum the needle passage is in fluid communication with the second portion.

24. The method according to claim 23 wherein the divider further comprises a screen, wherein the screen extends in the fluid passage, and wherein in step (a) the vapor phase of the substance passes through the screen.

25. The method according to claim 23 and prior to step (c) further comprising the step of rotating the container about the central axis with a rotating mechanism, wherein in the rotating step the rotating mechanism is operative to rotate the vial with the central axis extending generally horizontally.

26. The method according to claim 25 wherein in step (e) the analytical instrument includes a gas chromatograph.

* * * * *